US 6,572,557 B2

(12) United States Patent
Tchou et al.

(10) Patent No.: US 6,572,557 B2
(45) Date of Patent: Jun. 3, 2003

(54) SYSTEM AND METHOD FOR MONITORING PROGRESSION OF CARDIAC DISEASE STATE USING PHYSIOLOGIC SENSORS

(75) Inventors: Patrick Tchou, Cleveland, OH (US); Euljoon Park, Stevenson Ranch, CA (US); Kerry A. Bradley, Glendale, CA (US)

(73) Assignee: Pacesetter, Inc., Sylmar, CA (US)

( * ) Notice: Subject to any disclaimer, the term of this patent is extended or adjusted under 35 U.S.C. 154(b) by 163 days.

(21) Appl. No.: 09/746,235

(22) Filed: Dec. 21, 2000

(65) Prior Publication Data
US 2001/0037067 A1 Nov. 1, 2001

Related U.S. Application Data
(60) Provisional application No. 60/203,017, filed on May 9, 2000.

(51) Int. Cl.[7] .................................................. A61B 5/02
(52) U.S. Cl. ....................................................... 600/483
(58) Field of Search ................................. 600/483, 484, 600/485, 486, 487, 888, 508, 509, 510, 511, 512, 513; 607/18, 23

(56) References Cited

U.S. PATENT DOCUMENTS

| 5,476,483 A | * | 12/1995 | Bornzin et al. | 607/17 |
| 5,514,162 A | * | 5/1996 | Bornzin et al. | 607/19 |
| 5,902,324 A | * | 5/1999 | Thompson et al. | 607/9 |
| 6,129,744 A | * | 10/2000 | Boute | 600/516 |
| 6,277,078 B1 | * | 8/2001 | Porat et al. | 600/486 |

* cited by examiner

Primary Examiner—Mahmoud Gimie

(57) ABSTRACT

A system and corresponding method are provided to monitor physiological parameters associated with the progression, stabilization, or regression of symptoms of heart disease such as congestive heart failure (CHF). The monitoring is implemented by ongoing surrogate measurement of standard and direct measurements, such as daily activity and respiratory and cardiac rate response, utilizing existing implantable, rate-responsive stimulation devices that incorporate activity, respiration, and/or other sensors. The system includes a sensor that measures activity and/or minute ventilation when triggered by changes in the sensed intrinsic heart rate and/or changes in a sensor-indicated pacing rate.

25 Claims, 7 Drawing Sheets

SYSTEM AND METHOD FOR MONITORING PROGRESSION OF CARDIAC DISEASE STATE USING PHYSIOLOGIC SENSORS

This application claims the benefit of U.S. Provisional Application No. 60/203,017, filed May 9, 2000.

FIELD OF THE INVENTION

This invention relates generally to a programmable cardiac stimulation apparatus for the purpose of monitoring the progression of congestive heart failure or the efficacy of delivered heart failure therapies. More specifically, the present invention is directed to an implantable stimulation device and associated method for monitoring and analyzing physiological parameters indicative of overall patient well-being in order to provide diagnostic information for heart failure therapy optimization.

BACKGROUND OF THE INVENTION

Congestive heart failure (CHF) is a debilitating, end-stage disease in which abnormal function of the heart leads to inadequate blood flow to fulfill the needs of the body's tissues. Typically, the heart loses propulsive power because the cardiac muscle loses capacity to stretch and contract. Often, the ventricles do not adequately fill with blood between heartbeats and the valves regulating blood flow may become leaky, allowing regurgitation or back flow of blood. The impairment of arterial circulation deprives vital organs of oxygen and nutrients. Fatigue, weakness, and inability to carry out daily tasks may result. Not all CHF patients suffer debilitating symptoms immediately. Some may live actively for years. Yet, with few exceptions, the disease is relentlessly progressive.

As CHF progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output.

CHF has been classified by the New York Heart Association (NYHA). Their classification of CHF corresponds to four stages of progressively worsening symptoms and exercise capacity from Class I to Class IV. Class I corresponds to no limitation where ordinary physical activity does not cause undue fatigue, shortness of breath, or palpitation. Class II corresponds to slight limitation of physical activity where such patients are comfortable at rest, but where ordinary physical activity results in fatigue, shortness of breath, palpitations, or angina. Class III corresponds to a marked limitation of physical activity where, although patients are comfortable at rest, even less than ordinary activity will lead to symptoms. Class IV corresponds to inability to carry on any physical activity without discomfort, where symptoms of CHF are present even at rest and where increased discomfort is experienced with any physical activity.

Current standard treatment for heart failure is typically centered around medical treatment using ACE inhibitors, diuretics, and digitalis. It has also been demonstrated that aerobic exercise may improve exercise tolerance, improve quality of life, and decrease symptoms. Heart transplantation is an option, but only in 1 out of 200 cases. Other cardiac surgery may also be indicated, but only for a small percentage of patients with particular etiologies. Although advances in pharmacological therapy have significantly improved the survival rate and quality of life of patients, patients in NYHA Classes III or IV, who are still refractory to drug therapy, have a poor prognosis and limited exercise tolerance. Cardiac pacing has been proposed as a new primary treatment for patients with drug-refractory CHF.

By tracking the progression or regression of CHF more closely, treatments could be administered more effectively. Commonly, patients adapt their lifestyle and activities to their physical condition. The activity level of the patients with NYHA Class III or IV would be much lower than that of the patients with NYHA Class I or II. The change in lifestyle or activity level, due to the patient's heart condition, will be reflected by activity and respiration physiological parameters.

Besides various assessments of the cardiac function itself, assessment of activity and respiration are typically performed. This includes maximal exercise testing in which the heart rate and maximum ventilation are measured during peak exertion. However, peak exercise performance has been found to not always correlate well with improvements in a patient's clinical condition. Therefore, sub-maximal exercise testing can also be performed, such as a six-minute walk test. While improvements in sub-maximal exercise may suggest an improvement in clinical condition, sub-maximal exercise performance can be variable in that it is dependent on how the patient happens to be feeling on the particular day of the test.

To obtain a more general assessment of the patient's activity on a daily basis, patients are often asked to answer questionnaires regarding numerous aspects of daily life. Such questionnaires are inherently subjective. Nevertheless, collected information is useful to the physician. Since existing CHF treatments are palliative and not curative, a major goal in administering therapies is to improve the quality of daily life which is directly reflected by the level and variety of activities the patient is comfortable performing.

Thus, it would be desirable to have an objective means of chronically and non-invasively monitoring physiological parameters indicative of a patient's overall well-being on an ongoing, daily basis. This would enhance the physician's ability to optimize and carefully tailor therapies for stabilizing CHF.

A number of attempts have been made previously to provide for chronic monitoring of physiological parameters associated with CHF using implantable cardiac devices, such as pacemakers, in conjunction with physiological sensors. Reference is made to U.S. Pat. No. 5,518,001 to Snell; U.S. Pat. No. 5,944,745 to Rueter; U.S. Pat. No. 5,974,340 to Kadhiresan; U.S. Pat. No. 5,935,081 to Kadhiresan; U.S. Pat. No. 6,021,351 to Kadhiresan et al.; and U.S. Pat. No. 5,792,197 to Nappholz. Reference is also made to U.S. Pat. No. 4,901,725 to Nappholz, et al.; and U.S. Pat. No. 5,964,788 to Greenhut, that generally describe rate-responsive pacemakers using impedance measurements of respiration for controlling the pacing rate.

However, there is still an unsatisfied need for a method of chronically and objectively monitoring related physiological indicators of the severity of CHF, at time points representative of the overall patient condition, to thereby reflect a worsening or improving condition associated with therapy delivery. This method would also permit reporting and displaying resulting data in a way that is useful and informative to the physician.

SUMMARY OF THE INVENTION

One feature of the present invention to satisfy this need is to monitor physiological parameters associated with the progression, stabilization, or regression of symptoms of heart disease such as congestive heart failure (CHF). The monitoring is implemented by ongoing surrogate measurement of standard and direct measurements, such as daily activity and respiratory and cardiac rate response, utilizing existing implantable, rate-responsive stimulation devices that incorporate activity, respiration, and/or other sensors.

To further optimize CHF therapy, the present invention provides a method of processing the collected data and displaying relationships of the measured parameters in a way that is diagnostically meaningful to the physician. These goals are achieved without significant memory requirements, complex circuitry, or additionally implanted hardware.

In one embodiment of the present invention, a piezoelectric accelerometer measures activity (ACT) when triggered by changes in the sensed intrinsic heart rate (HR), or changes in a sensor-indicated pacing rate (SIR). In another embodiment, the present invention uses an impedance measurement to monitor respiration, more specifically to monitor increases in minute ventilation (MV) above an average resting minute ventilation, when triggered by changes in the sensed heart rate or changes in the sensor-indicated pacing rate. The activity and the minute ventilation data can be collected simultaneously, such that the level of daily activities can be correlated to both respiratory and cardiac rate responses.

Another aspect of the present invention is to provide a method for processing and displaying the measured activity or minute ventilation data to interpolate diagnostic relationships between activity, minute ventilation, heart rate, or sensor-indicated pacing rate, that are representative of the overall well-being of the patient, thus reflective of the severity of CHF symptoms. Activity and minute ventilation data collected upon each heart rate or sensor-indicated pacing rate change are stored in histogram bins assigned to defined heart rate or sensor-indicated pacing rate ranges. After a given period of data collection, such as 24 hours, the data for each rate range is averaged and statistical or mathematical analysis is performed to determine correlation or regression coefficients that define the relationships between activity, heart rate, sensor-indicated pacing rate, or minute ventilation. Storing the averages and the relationship coefficients allows for future graphical display of the periodic data and frees memory bins for the next data collection time interval.

Thus, a further aspect of the present invention is a method that allows data to be downloaded and displayed in a diagnostically meaningful way during a routine office visit without requiring significant technical expertise and without additional invasive, time-consuming or expensive procedures. Such diagnostic data are valuable to a physician in adjusting medical or pacing therapies for the treatment of CHF.

Another aspect of the present invention allows for metabolic monitoring when neither the intrinsic heart rate nor the sensor-indicated pacing rate is available, e.g., during fixed rate pacing modes. During such modes, changes in the level of one sensed parameter, for example activity, can be used to trigger collection and data storage of one or more other sensed parameters, for example minute ventilation. In this way, a change in activity level triggers collection of minute ventilation data that are stored in memory according to defined ranges of activity. Minute ventilation and activity data can thus be collected, and an inter-relationship determined and graphically displayed during periods of fixed rate pacing.

BRIEF DESCRIPTION OF THE DRAWINGS

The above and further features, advantages and benefits of the present invention will be apparent upon consideration of the present description taken in conjunction with the accompanying drawings, in which.

DETAILED DESCRIPTION OF THE PREFERRED EMBODIMENTS

The following description is of a best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
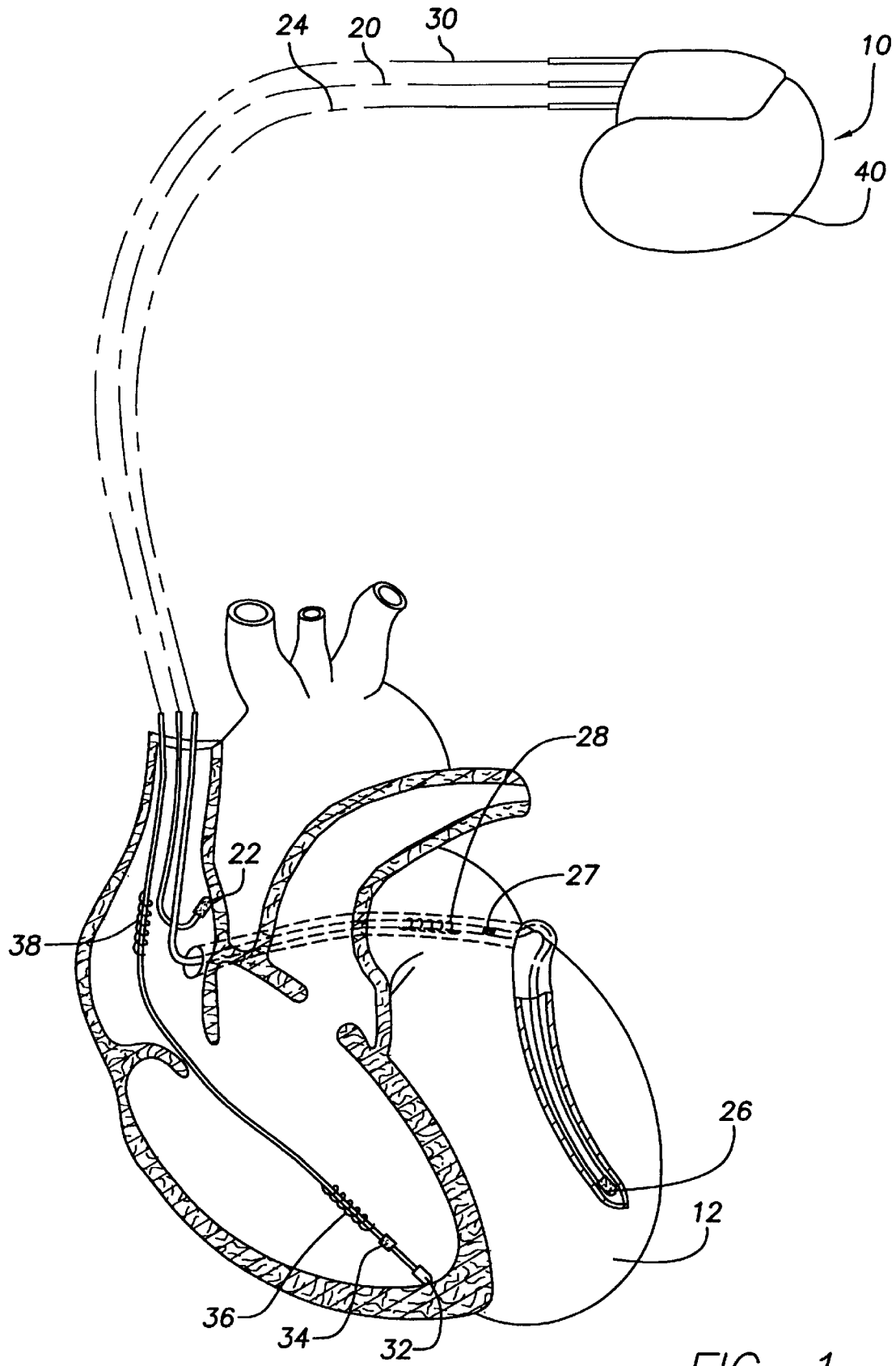
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus os so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, refer to U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, entitled "Coronary Sinus Lead with Atrial Sensing Capability" (Helland), which patent application and patent, respectively, are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
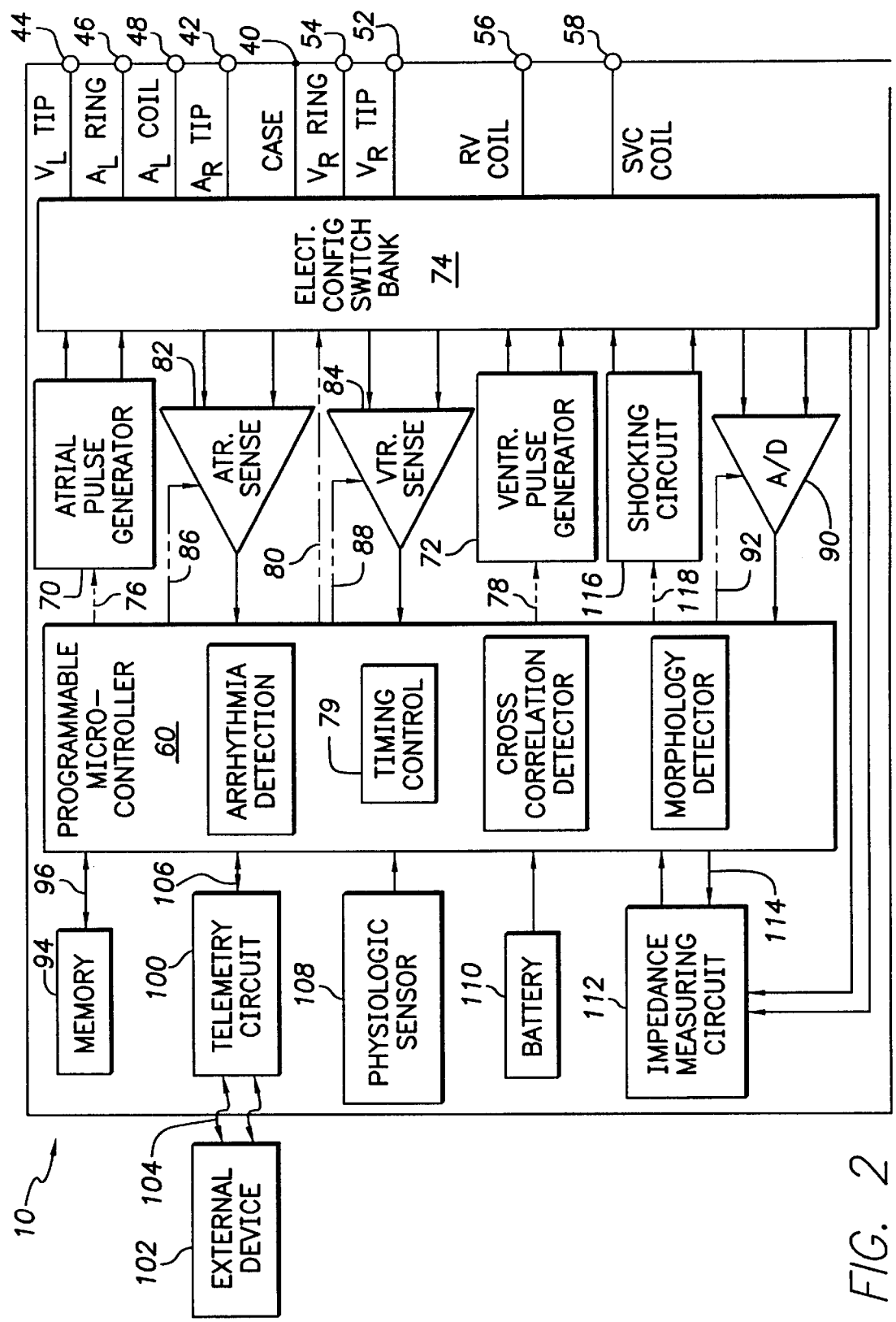
FIG. 2 is a functional block diagram of the multi-chamber implantable stimulation device of FIG. 1, illustrating the basic elements that provide cardioversion, defibrillation and/or pacing stimulation in four chambers of the heart.

FIG. 2 illustrates a simplified block diagram of the multi-chamber implantable stimulation device 10 which is capable of treating both fast and slow arrhythmias with stimulation therapy, including cardioversion, defibrillation, and pacing stimulation. While a particular multi-chamber device is shown, this is for illustration purposes only and one of skill in the art could readily duplicate, eliminate or disable the appropriate circuitry in any desired combination to provide a device capable of treating the appropriate chamber (s) with cardioversion, defibrillation and/or pacing stimulation.

The stimulation device 10 includes a housing 40 which is often referred to as a "can", "case" or "case electrode", and which may be programmably selected to act as the return electrode for all "unipolar" modes. The housing 40 may further be used as a return electrode alone or in combination with one or more of the coil electrodes 28, 36, or 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal 42 adapted for connection to the right atrial ($AR_D$) tip electrode 22.

To achieve left chamber sensing, pacing and/or shocking, the connector includes at least a left ventricular ($V_L$) tip terminal 44, a left atrial ($A_L$) ring terminal 46, and a left atrial ($A_L$) shocking terminal (coil) 48, which are adapted for connection to the left ventricular tip electrode 26, the left atrial ring electrode 27, and the left atrial coil electrode 28, respectively.

To support right chamber sensing, pacing and/or shocking, the connector further includes a right ventricular ($V_R$) tip terminal 52, a right ventricular ($V_R$) ring terminal 54, a right ventricular (RV) shocking terminal (coil) 56, and an SVC shocking terminal (coil) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry or processor, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art.

Representative types of control circuitry that may be used with the present invention include the microprocessor-based control system of U.S. Pat. No. 4,940,052 (Mann et al.), and the state-machines of U.S. Pat. No. 4,712,555 (Thornander et al.) and U.S. Pat. No. 4,944,298 (Sholder). For a more detailed description of the various timing intervals used within the stimulation device and their inter-relationship, refer to U.S. Pat. No. 4,788,980 (Mann et al.). These patents (U.S. Pat. Nos. 4,940,052; 4,712,555; 4,944,298; and 4,788,980) are incorporated herein by reference.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, ventricular interconduction (V—V) delay, pacing mode, etc.), as well as to keep track of the timing of refractory periods, PVARP intervals, noise detection windows, evoked response windows, alert intervals, marker channel timing, etc.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch bank 74 determines the "sensing polarity" of the cardiac signal by selectively closing the appropriate switches. In this way, the clinician may program the sensing polarity independent of the stimulation polarity.

Each of the sensing circuits, 82 and 84, preferably employ one or more low power, precision amplifiers with programmable gain and/or automatic gain control, bandpass filtering, and a threshold detection circuit, to selectively sense the cardiac signal of interest. The automatic gain control enables the stimulation device 10 to deal effectively with the difficult problem of sensing the low amplitude signal characteristics of atrial or ventricular fibrillation.

For a more complete description of a typical sensing circuit, refer to U.S. Pat. No. 5,573,550, entitled "Implantable Stimulation Device having a Low Noise, Low Power, Precision Amplifier for Amplifying Cardiac Signals" (Zadeh et al.). For a more complete description of an automatic gain control system, refer to U.S. Pat. No. 5,685,315, entitled "Cardiac Arrhythmia Detection System for an Implantable Stimulation Device" (McClure et al.). These patents (U.S. Pat. Nos. 5,573,550; and 5,685,315) are hereby incorporated herein by reference.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry (not shown), and the timing of any blocking circuitry (not shown) coupled to the inputs of the atrial and ventricular sensing circuits 82 and 84.

For arrhythmia detection, the stimulation device 10 utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60 or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing circuitry within the microcontroller 60, and enabling the data acquisition system 90 via control signal 92 to sample the cardiac signal that falls in the capture detection window and, based on the amplitude of the sampled cardiac signal, determines if capture has occurred.

The microcontroller 60 is further coupled to a memory 94 by a suitable data/address bus 96, where the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, pacing mode, and the amplitude, waveshape and vector of each shocking pulse to be delivered to the patient's heart 12 within each respective tier of therapy. A feature of the stimulation device 10 is the ability to sense and store a relatively large amount of data (e.g., from the data acquisition system 90), which data may then be used for subsequent analysis to guide the programming of the stimulation device 10.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through an established communication link 104. For examples of such devices, refer to U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. patent application Ser. No. 09/223,422, filed Dec. 30, 1998, entitled "Efficient Generation of Sensing Signals in an Implantable Medical Device such as a Pacemaker or ICD" (McClure et al.), all of which are hereby incorporated herein by reference.

In a preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) which control how and when the atrial and ventricular pulse generators 70 and 72 generate stimulation pulses.

While the physiologic sensor 108 is shown as being included within the stimulation device 10, it is to be understood that the physiologic sensor 108 may alternatively be external to the stimulation device 10, yet still be implanted within or carried by the patient. A common type of rate-responsive sensor is an activity sensor, such as an accelerometer or a piezoelectric crystal, which is mounted within the housing 40 of the stimulation device 10. Other types of physiologic sensors are also known, for example, sensors that sense the oxygen content of blood, pressure, cardiac output, ejection fraction, stroke volume, end diastolic volume, end systolic volume, respiration rate and/or minute ventilation, pH of blood, ventricular gradient, etc. However, any sensor may be used which is capable of sensing a physiological parameter that corresponds to the exercise state of the patient.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time and also be capable of providing high-current pulses (for capacitor charging) when the patient requires a shock pulse. The battery 110 must preferably have a predictable discharge characteristic so that elective replacement time can be detected. Accordingly, the stimulation device 10 can employ lithium/silver vanadium oxide batteries.

The stimulation device 10 further includes a magnet detection circuitry (not shown), coupled to the microcontroller 60. The purpose of the magnet detection circuitry is to detect when a magnet is placed over the stimulation device 10, which magnet may be used by a clinician to perform various test functions of the stimulation device 10 and/or to signal the microcontroller 60 that an external programmer 102 is in place to receive or transmit data to the microcontroller 60 through the telemetry circuit 100.

As further shown in FIG. 2, the stimulation device 10 is shown as having an impedance measuring circuit 112 which is enabled by the microcontroller 60 via a control signal 114. Certain applications for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of the valves, etc. The impedance measuring circuit 112 is advantageously coupled to the switch bank 74 so that any desired electrode may be used.

It is a primary function of the stimulation device 10 to operate as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high (11–40 joules) energy, as controlled by the microcontroller 60. Such shocking pulses are applied to the patient's heart through at least two shocking electrodes, as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28 (e.g., using the RV electrode as a common electrode).

Cardioversion shocks are generally considered to be of low to moderate energy level (so as to minimize pain felt by the patient), and/or synchronized with an R-wave, and/or pertaining to the treatment of tachycardia. Defibrillation shocks are generally of moderate to high energy level (i.e., corresponding to thresholds in the range of 5–40 joules), delivered asynchronously (since R-waves may be too disorganized) and pertaining exclusively to the treatment of fibrillation. Accordingly, the microcontroller 60 is capable of controlling the synchronous or asynchronous delivery of the shocking pulses.

Figure 3:
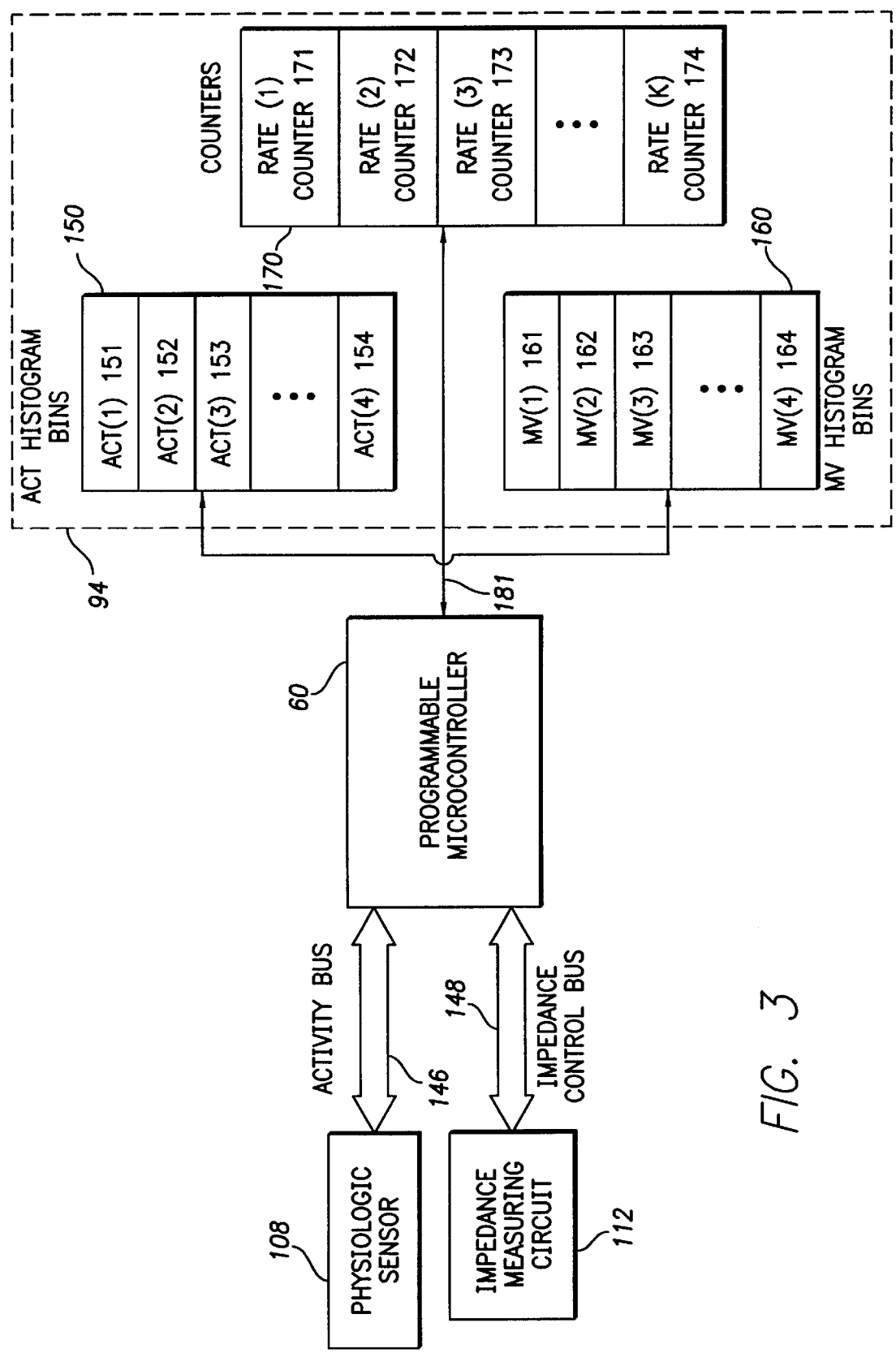
FIG. 3 is a block diagram of circuitry used in the stimulation device of FIG. 1 for automatically and reliably measuring metabolic parameters correlated to the severity of heart failure, in accordance with the present invention.

In FIG. 3, a flow chart is shown describing an overview of the operation and features implemented in one embodiment of the stimulation device 10. In this flow chart and the other flow charts described herein, the various algorithmic steps are summarized in individual "blocks". Such blocks describe specific actions or decisions that must be made or carried out as the algorithm proceeds. Where the microcontroller 60 (or its equivalent) is employed, the flow charts presented herein provide the basis for a "control program" that may be executed or used by such a microcontroller 60 (or its equivalent) to effectuate the desired control of the stimulation device.

In this embodiment, the control program is comprised of multiple integrated program modules with each module bearing responsibility for controlling one or more functions of the stimulation device 10. For example, one program module may control the delivery of stimulating pulses to the heart 12, while another may control the verification of ventricular capture and ventricular pacing energy determination. In effect, each program module is a control program dedicated to a specific function or set of functions of the stimulation device 10.

With further reference to FIG. 3, the physiologic sensor 108 is comprised, for example, of a piezoelectric accelerometer-type sensor secured to, or within, the case 40. It should be clear that any other suitable sensor that provides a response to physical activity may alternatively be used. Reference is made to U.S. Pat. Nos. 5,425,750 and 5,383,473 that are incorporated herein by this reference. The accelerometer may be a single axis device, but preferably it is capable of sensing accelerations along three axes.

The physiologic sensor 108 responds to movement and vibrations reaching it by emitting an electrical signal, thereby producing an analog signal correlated to the patient's activity. The output of the physiologic sensor 108 is applied to signal processing circuitry forming part of the microcontroller 60 (FIG. 2), which may include filtering, amplifying and wave shaping components. The signal processing circuitry of the microcontroller 60 receives the activity based signals from the physiologic sensor 108 along activity data bus 146.

The stimulation device 10 also makes an impedance measurement when the microcontroller 60 sends a signal on an impedance control bus 148 to activate the impedance measuring circuit 112. The impedance measuring circuit 112 then applies a current to the corresponding cardiac leads and measures a voltage resulting from the applied current. These current and voltage signals define an impedance characteristic of the patient's metabolic demand and, more particularly, of the instantaneous minute ventilation which is a function of the respiration rate and the tidal volume. This instantaneous minute ventilation is then filtered and further modified by subtracting it from a long-term average value. The resulting parameter is the minute ventilation parameter. The minute ventilation parameter is converted by the microcontroller 60 into a base pacing parameter, such as a metabolic rate.

In accordance with the present invention, the memory 94 (FIG. 2) is used to store activity and respiration data over an extended period of time, for example a period of weeks or months. Data to be stored are written to the memory 94 through the data/address bus 96 from the microcontroller 60. The microcontroller 60 executes programs stored in the memory 94 using the activity and impedance data to calculate mathematical relationships between activity, respiration, and heart rate or sensor-indicated pacing rate. The results are stored in the memory 94 and are available to a medical practitioner for diagnosing the progression or regression of CHF symptoms and selecting therapeutic interventions.

The telemetry circuit 100 provides a bi-directional link between the microcontroller 60 and the external device 102. It allows data such as the operating parameters to be read from, or altered by, the stimulation device 10. The telemetry circuit 100 may be employed for transmitting the activity and minute ventilation data stored in the memory 94 to the external programmer 102 for display. Parameters used by the microcontroller 60 in sampling the activity and minute ventilation data as well as parameters used in programs stored in the memory 94, which are called upon by the microcontroller 60 during the analysis of the collected data, may also be programmed via the telemetry circuit 100.

The stimulation device 10 acquires measurements of numerous physiological parameters that reliably indicate the severity of the heart failure. In one embodiment of the present invention, the stimulation device 10 employs the accelerometer sensor 108 to measure the physical activity, thereby reflecting a patient's feeling of well-being.

In another embodiment, the impedance measuring circuit 112, which measures the thoracic impedance to determine the respiratory minute ventilation as described generally in U.S. Pat. No. 4,901,725 which is incorporated herein by reference, can be used in place of, or in conjunction with, the physiologic sensor 108 as an indication of well-being.

Having described the environment in which the stimulation device 10 is used, the operation of stimulation device 10 in accordance with exemplary embodiments of the present invention will now be described in connection with FIGS. 3 through 7.

Referring to FIG. 3, the stimulation device 10 utilizes ACT histogram bins 150 for storing activity data and MV histogram bins 160 for storing minute ventilation data. Additionally, the stimulation device 10 utilizes a number of counters 170 to track the number of data samples stored in each of the histogram bins 150 and 160. The histogram bins, 150 and 160, and the counters 170 are preferably located in the memory 94.

Each of the histogram bins 150 and 160 and the counters 170 are assigned to a specific heart rate range. For example, ACT histogram bin ACT(1) 151, MV histogram bin MV(1) 161, and counter (1) 171 are assigned to heart rates falling within the range of the base rate through the "base rate+N", where N equals, for example, 10 ppm, and the base rate is the base pacing rate as determined by the operating parameters of the stimulation device 10. Likewise, ACT histogram bin ACT(2) 152, MV bin MV(2) 162, and counter(2) 172 are assigned to the "base rate+N" through the "base rate+2*N". Generally, an ACT histogram bin designated by ACT(K), a MV histogram bin designated by MV(K), and counter(K) are assigned to the "base rate+(K−1)*N" through the "base rate+K*N". The resolution of these heart rate ranges can be made adjustable by designating N as a programmable value.

When one of the ACT histogram bins 150 is enabled according to a method of operation 200 yet to be described in connection with FIG. 4, the activity data sensed by the physiologic sensor 108 is transmitted along an address and data bus 181 to the microcontroller 60 and is accumulated in the corresponding bin in the memory 94. Likewise, when one of the MV histogram bins 160 is enabled pursuant to the method of operation 200, the minute ventilation data sensed by the impedance measuring circuit 112 is accumulated in the corresponding bin the memory 94 by the microcontroller 60.

Figure 4:
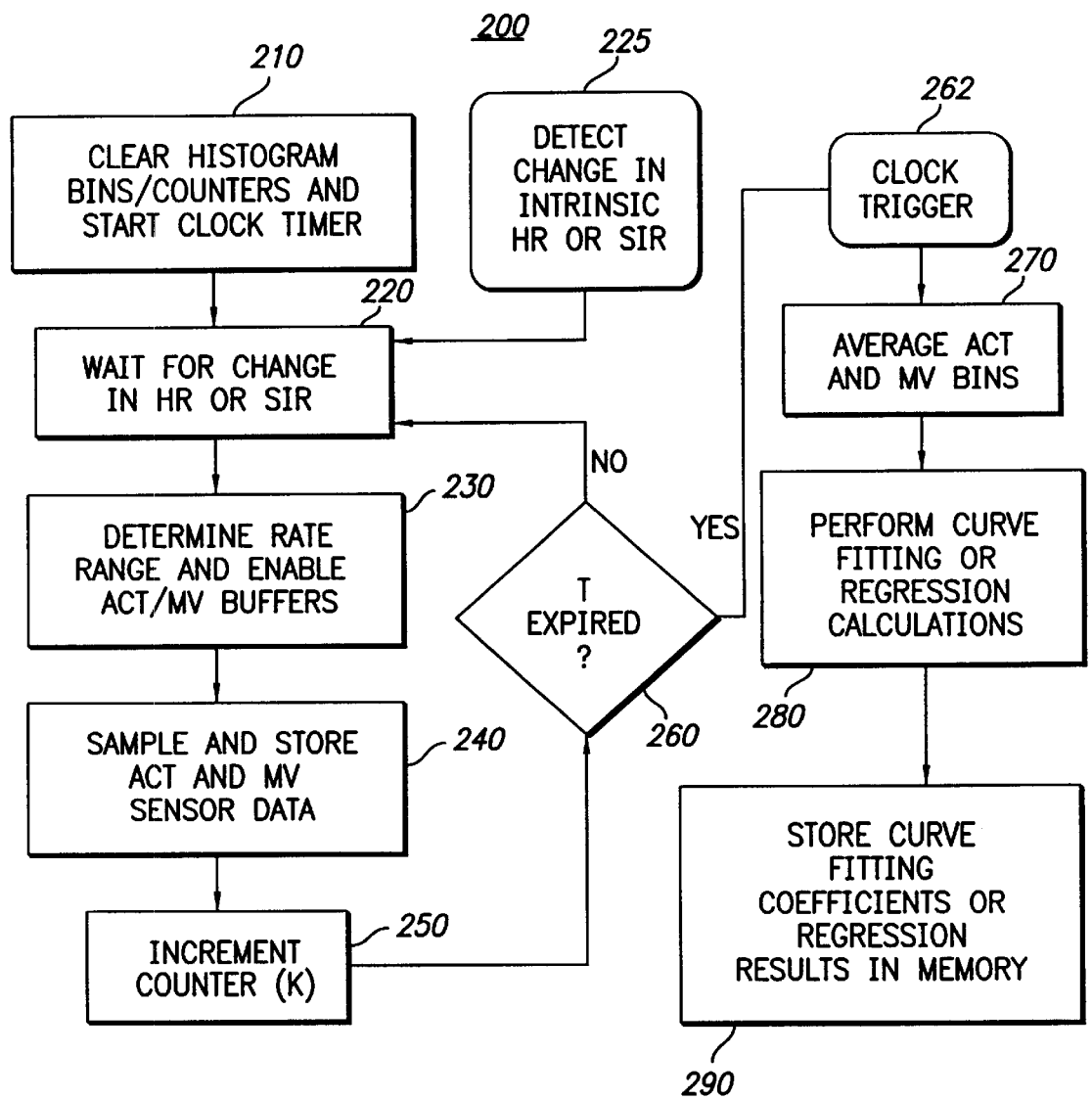
FIG. 4 is a flow diagram that illustrates the operation of the circuitry of FIG. 3 for sampling, storing, and processing metabolic parameters correlated to the severity of heart failure symptoms, in accordance with the present invention.

Referring now to FIG. 4, the method of operation 200 can be activated manually via the external device 102 through the telemetry circuit 100. The method 200 begins by setting all counters 170 to zero and clearing the histogram bins 150 and 160. The method 200 then waits at step 220 for a change in the intrinsic heart rate as determined by the microcontroller 60 based on inputs from the atrial sensor 82 (FIG. 2) and/or the ventricular sensor 84 (FIG. 2). Once a change in the heart rate (HR) is detected at step 225, the method 200 proceeds to step 230 where it determines the range K that the new heart rate falls into and enables the appropriate ACT histogram bins 150 and MV histogram bins 160.

At step 240, the activity level, as determined by the physiologic sensor 108 (FIG. 2), is written to the appropriate histogram bin ACT(K) in the ACT histogram bins 150 (FIG. 3). Additionally, at step 240, the minute ventilation, as determined by the impedance measuring circuit 112, is written to the appropriate MV histogram bin MV(K) of the MV histogram bins 160 (FIG. 3).

Following data collection, the appropriate counter (K) of the series of counters 170 (FIG. 3) is incremented at step 250 in order to count the number of times data is written to the Kth histogram bin of the ACT histogram bins 150 and the MV histogram bins 160, thus providing the sample number needed for statistical calculations to be made on the data.

Data collection continues upon each heart rate (HR) change during a given period of time T, which is programmable, e.g., to a time period of 24 hours. The method 200 determines at step 260 if the period T has expired and then, if it has not, the method 200 returns to step 220 and repeats steps 230, 240, and 250 as described above.

Once the method 200 determines at step 260 that the period T has expired, a clock trigger initiates the processing of the collected data at step 262. Alternatively, if the available memory of any given bin is full before the period T expires, the processing of the collected data may be initiated and then the actual data collection period would be logged.

Upon receiving the clock trigger at step 262, the microcontroller 60 using programs stored in the memory 94 performs, at step 270, statistical and mathematical operations on the activity and minute ventilation data retrieved from the corresponding ACT histogram bins 150 and MV histogram bins 160, respectively, via the address and data bus 181 (FIG. 3). A number of statistical or mathematical operations could be performed. For example, in one embodiment, the mean values of the activity and minute ventilation for each heart rate range are calculated at step 270 using the corresponding counter values as the sample numbers.

The mean activity and minute ventilation values for each heart rate range are then stored in the memory 94 and are further used to determine mathematical relationships between the measured activity, minute ventilation, and heart rate at step 280. Preferably, the microprocessor 60 performs curve-fitting and/or regression analysis on the averaged data to determine the relationships between the activity and minute ventilation parameters, as well as between each of these parameters and the heart rate.

At step 290, the curve-fitting coefficients and/or regression results are also stored in the memory 94 for future display. By storing only descriptive statistics and correlation or regression coefficients, minimal memory is required and the histogram bins 150, 160 can be cleared to allow for more data collection. Therefore, after completing step 290, the method 200 returns to step 210 where the histogram bins 150, 160, and the counters 170 are cleared and a clock timer is reset in preparation for collecting data for the next time interval T.

Figure 5:
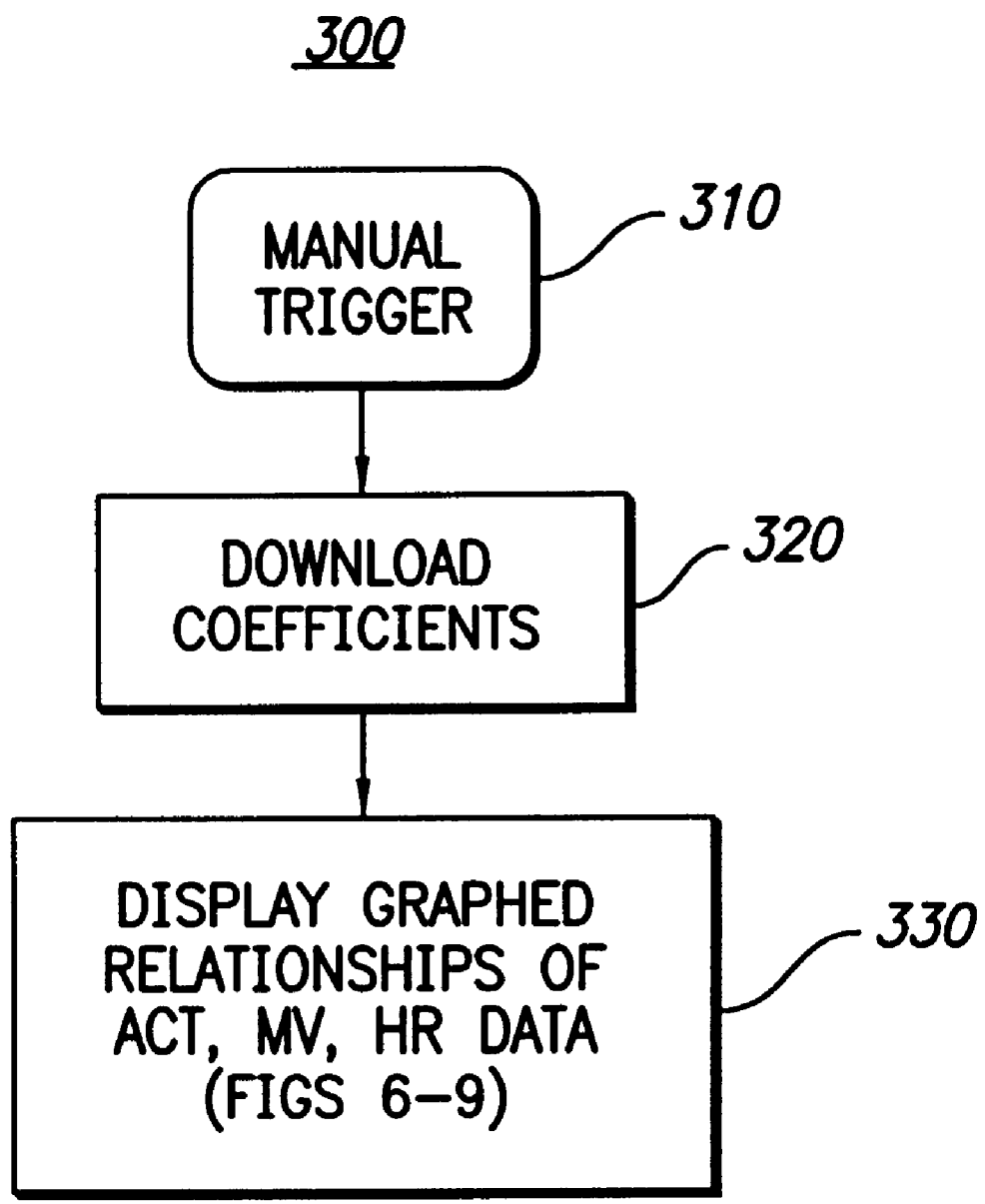
FIG. 5 is a flow diagram illustrating the operation of the stimulation device of FIG. 1 for displaying the processed data produced by the operation of FIG. 4.

Referring now to FIG. 5, it illustrates a method 300 for displaying the data processed by the method of operation 200 of FIG. 4. The results stored at step 290 (FIG. 4) are downloaded at step 320 upon receiving a manual trigger 310 (e.g., during an office visit) from the external device 102 (FIG. 2) and displayed at step 330 on a monitor in graphical form, so that trends can be observed. Examples of the relationships of the measured parameters and how the data may be displayed are depicted graphically in FIGS. 6–9, will now be described in detail.

Figure 6:
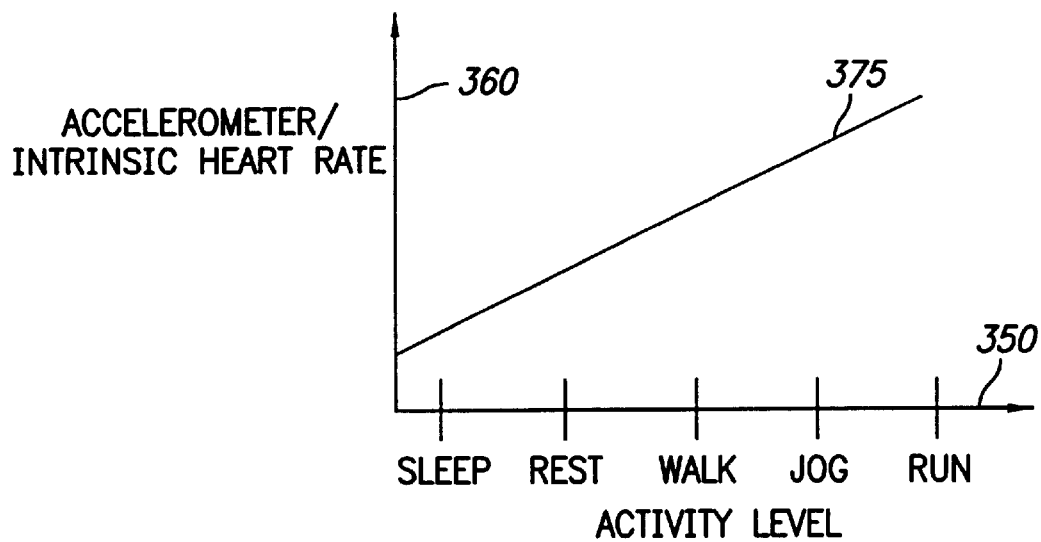
FIGS. 6, 7, 8 and 9 are graphs depicting the relationships between the measured parameters, and illustrating exemplary displays generated by the operation of FIG. 5 in accordance with the present invention.

The graph shown in FIG. 6 depicts the underlying principle of an accelerometer measurement. When the patient's physical activity level, represented on the axis 350, increases, the accelerometer output, represented on the axis 360, likewise increases. The accelerometer output and the patient activity have a positive linear relationship as represented by the graph 375. Since the accelerometer output can be used as a direct measure of a patient's activity, general well-being is also measured indirectly, since the level of activity a patient engages in on an ongoing day-to-day basis will depend on his or her comfort during exertion. A preferred embodiment of the present invention thus uses the activity level measurement as an indication of the severity of CHF.

The normal physiological response to an increase in physical activity is an increase in the intrinsic heart rate. This positive linear relationship can also be represented by the graph 375 of FIG. 6 in which the intrinsic heart rate represented along the axis 360 would increase as the patient's activity represented along the axis 350 increases. The degree to which the heart rate increases in response to exertion, however, may also reflect disease state. If the heart pumping function becomes compromised as in the state of CHF, the heart rate may have to increase by a greater amount than normal in order to compensate for low blood ejection, in order to still meet the metabolic needs of the body. In this situation, the slope of the graph 375 would increase.

Some patients may also experience an inadequate heart rate response to exercise. In this case, the intrinsic heart rate does not increase enough to meet the metabolic demand. In this situation, a sensor-indicated pacing rate may be applied such that a metabolically appropriate heart rate is maintained. Such a sensor-indicated pacing rate can be based on accelerometer sensing of activity, impedance measurements of respiration, or any other sensor.

For each change in the activity, an MV histogram bin 160 is enabled to store a minute ventilation data and the corresponding counter 170 is incremented. Relationships between activity and minute ventilation can then be determined by the method 200 illustrated in FIGS. 4 and 5.

Figure 7:
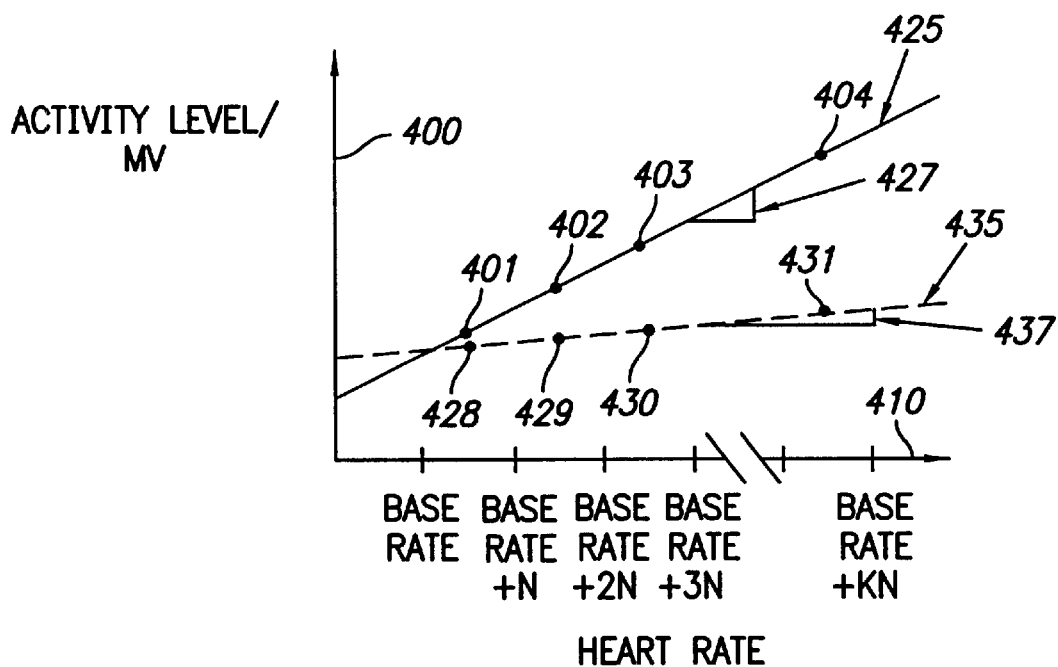

Whenever a physician wishes to review the activity or minute ventilation measurements, the external device 102 may be used to interrogate the implanted stimulation device 10 via the telemetry circuit 100 and graphically display the stored data from step 290 of FIG. 4. In one embodiment of the present invention, the resulting relationship of activity level and minute ventilation with the heart rate is displayed graphically as illustrated by FIG. 7. Activity level (or minute ventilation) is plotted on the axis 400 and is expected to increase with increasing heart rate which is plotted on the axis 410. Each one of the points 401, 402, 403, 404, 428, 429, 430, and 431, plotted along the two exemplary graphs 425, 435, represents the average activity calculated for the Kth memory bin of the ACT histogram bins 150. The graphs 425 and 435, joining the plotted averages, illustrate the positive relationship, which is shown to be linear in this example, between the heart rate and activity (or minute ventilation). From this relationship, a slope can be determined. If the slope, (e.g., slope 437) is low, such that the graph 435 is relatively flat, little change in activity occurs indicating the patient's condition is deteriorating. If, however, the slope (e.g., slope 427) is high, such that graph 425 is relatively steep, a greater range of activity levels is presumed to occur confirming the well-being of the patient.

Respiratory function will also be affected by the severity of CHF. Shortness of breath during even low-level exertion is a common symptom. Therefore, the relationship between activity and respiration is also diagnostically important. When both the minute ventilation and activity are acquired, therefore, the microcontroller 60 will also calculate the relationship between the minute ventilation and the activity as indicated by step 280 of FIG. 4. A worsening in CHF is indicated by increased activity (e.g., the slope 427 is relatively steep) without an appropriate increase in respiration (e.g., the slope 437 is relatively flat).

Figure 8:
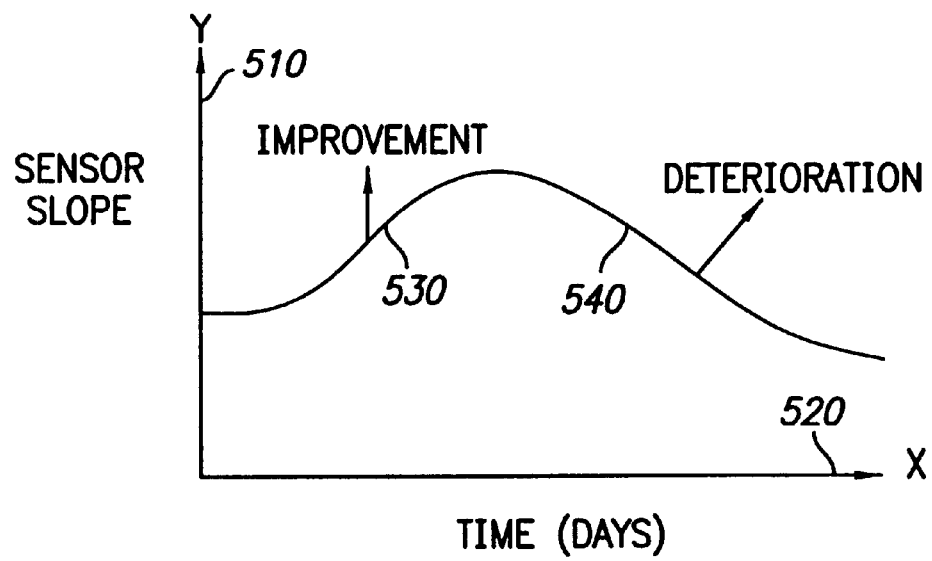

The relationship between the heart rate and activity (or minute ventilation), as exemplified by the slopes 427 and 437, is displayed graphically over time in FIG. 8. When the slope relationship, plotted with respect to the Y-axis 510, is increasing over time plotted on the X-axis 520, as indicated by the graph section 530, the patient's well-being is presumed to be improving. When the slope relationship is decreasing over time, as indicated by the graph section 540, the patient's well-being is presumed to be declining. This direct indication of clinical condition indirectly represents the severity of heart failure, and importantly represents the target of heart failure therapies, i.e., to improve clinical condition and quality of life. Therefore, the information depicted in FIG. 8 is valuable to a clinician in adjusting medical dosages or pacing parameters.

The method of operation 200 of FIG. 4 has been described based on ranges of the sensed heart rate. However, if the intrinsic heart rate is not available, for example, when the pacemaker is pacing according to a sensor-indicated pacing rate (SIR) from one sensor, then the sensor-indicated pacing rate is similarly divided into rate ranges of resolution N ppm. Changes in the sensor-indicated pacing rate can then be used to trigger the collection of the other sensor data in the method 200. The activity and minute ventilation data, or other available sensor data, would then be processed and related to the sensor-indicated pacing rate rather than to the intrinsic heart rate in the method 200.

Figure 9:
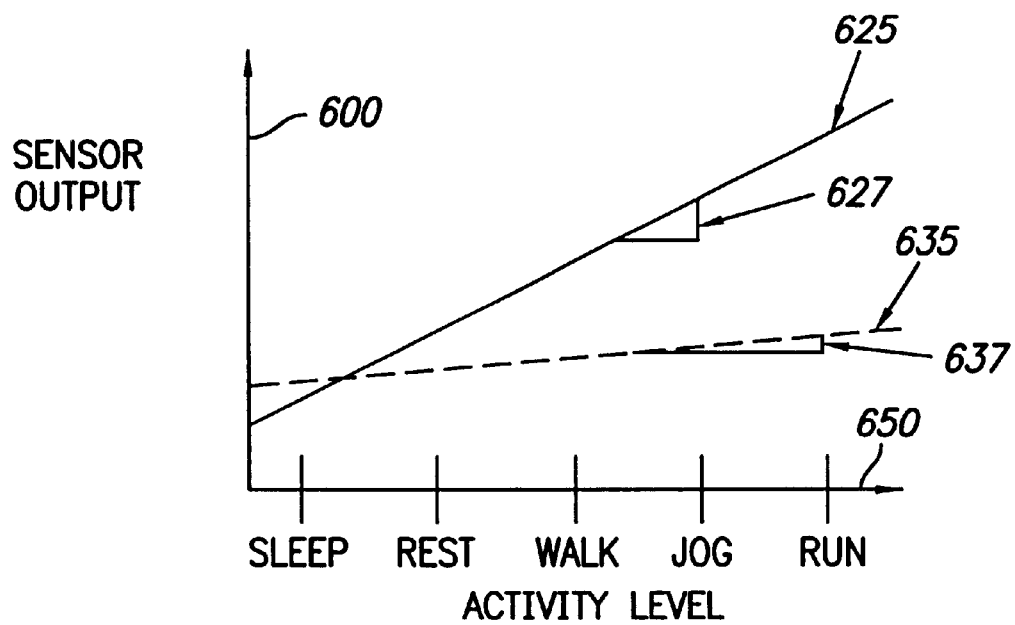

With reference to FIG. 9, if neither the intrinsic heart rate nor the sensor-indicated pacing rate is available because, for example, the stimulation device 10 is programmed in such a way that automatic adjustment of the pacing rate is disabled, then a "surrogate" parameter for either the heart rate or the sensor-indicated pacing rate may be provided in the form of an activity level parameter, e.g., measured by an accelerometer. The output of the physiologic sensor 108 (e.g., not an accelerometer in this case) is then plotted against the "surrogate" parameter.

The slopes (i.e., 627 and 637) of the resulting linear graphs (i.e., 625 and 635) are calculated as explained earlier, and plotted as illustrated in FIG. 8, for display to the practitioner.

While the invention has been described with reference to particular embodiments, modifications could be made thereto by those skilled in the art without departing from the spirit and scope of the invention. For example, the relationships depicted in FIGS. 6 through 8 are for illustrative purposes and other physiological parameters or different aspects of those parameters and their inter-relationships could also be employed by the present invention.

What is claimed is:

1. A system for automatically monitoring the progression of a patient's cardiac condition, comprising:
   a sensor for measuring the patients heart rate;
   a physiologic sensor for measuring the patient's physiologic data;
   a memory for storing the patient's physiologic data with respect to the patient's heart rate;
   a processor for calculating differential changes in the patient's physiologic data stored in the memory relative to incremental changes in the patient's heart rate; and wherein
   the processor correlates the differential changes to the progression of the patient's cardiac condition.

2. The system as recited in claim 1, wherein the physiologic sensor measures data corresponding to the patient's activity level in response to the patient's heart rate and the processor calculates differential changes in the patient's activity data relative to incremental changes in the patient's heart rate.

3. The system as recited in claim 2, wherein the physiologic sensor measures data corresponding to the patient's activity level in response to the patient's intrinsic heart rate and the processor calculates differential changes in the patient's activity data relative to incremental changes in the patient's intrinsic heart rate.

4. The system as recited in claim 3, wherein the processor averages the patient's activity data for selected intrinsic heart rate changes.

5. The system as recited in claim 1, wherein the physiologic sensor includes an activity sensor.

6. The system as recited in claim 5, wherein the activity sensor includes an accelerometer.

7. The system as recited in claim 6, wherein the accelerometer includes a piezoelectric-type accelerometer.

8. The system as recited in claim 5, wherein the activity sensor further measures the patient's activity levels in response to changes in a patient's sensor-indicated pacing rate.

9. The system as recited in claim 1, wherein the physiologic sensor further includes a sensor for measuring a patient's respiratory minute ventilation.

10. The system as recited in claim 1, wherein the physiologic sensor includes one or more sensors that measure one or more of:
    oxygen content of blood, pressure, cardiac output, ejection fraction, stroke volume, end diastolic volume, end systolic volume, respiration rate and/or minute ventilation, pH of blood, or ventricular gradient.

11. The system as recited in claim 1, wherein the memory includes a plurality of histogram bins for storing the activity data; and wherein each histogram bin is assigned to a specific heart rate range.

12. A system for automatically monitoring the progression of a patient's cardiac condition, comprising:
    a sensor for measuring the patient's intrinsic heart rate;
    a physiologic sensor for measuring the patient's minute ventilation data;
    a memory for storing the patient's minute ventilation data with respect to the patient's heart rate;
    a processor for calculating differential changes in the patient's minute ventilation data stored in the memory relative to incremental changes in the patient's heart rate; and wherein
    the processor correlates the differential changes to the progression of the patient's cardiac condition.

13. A system for use with a stimulation device to automatically monitor the progression of a patient's cardiac condition, comprising:
    a sensor for measuring a stimulation rate of the stimulation device;
    a physiologic sensor for measuring the patient's activity data;
    a memory for storing the patient's activity data with respect to the stimulation rate;
    a processor for calculating differential changes in the patient's activity data stored in the memory relative to incremental changes in the stimulation rate; and wherein
    the processor correlates the differential changes to the progression of the patient's cardiac condition.

14. A system for automatically monitoring the progression of a patient's cardiac condition, comprising:
    a sensor for measuring the patient's activity data;
    a physiologic sensor for measuring the patient's physiologic data;
    a memory for storing the patient's physiologic data with respect to the patient's activity data;
    a processor for calculating differential changes in the patient's physiologic data stored in the memory relative to incremental changes in the patient's activity data; and wherein
    the processor correlates the differential changes to the progression of the patient's cardiac condition.

15. A method for automatically monitoring the progression of a patient's cardiac condition, comprising:
    measuring the patient's intrinsic heart rate;
    measuring the patient's activity data;
    storing the patient's activity data with respect to the patient's heart rate;
    calculating differential changes in the patient's activity data relative to incremental changes in the patient's heart rate; and
    correlating the differential changes to the progression of the patient's cardiac condition.

16. A system for automatically monitoring the progression of a patient's cardiac condition, comprising:
    means for measuring the patient's intrinsic heart rate;
    means for measuring the patient's activity data;
    a memory for storing the patient's activity data with respect to the patient's heart rate;
    calculating means for calculating differential changes in the patient's activity data stored in the memory relative to incremental changes in the patient's heart rate; and wherein the calculating means correlates the differential changes to the progression of the patient's cardiac condition.

17. A system for automatically monitoring the progression of a patient's cardiac condition, comprising:

a sensor for measuring the patient's heart rate;

a physiologic sensor for measuring the patient's physiologic data, the patient's physiologic data stored in the memory in response to a change in the patient's heart rate;

a memory for storing the patient's physiologic data with respect to the patient's heart rate;

a processor for calculating differential changes in the patient's physiologic data stored in the memory relative to incremental changes in the patient's heart rate; and wherein the processor correlates the differential changes to the progression of the patient's cardiac condition.

18. The system as recited in claim 17, wherein the physiologic sensor measures data corresponding to the patient's activity level in response to the patient's heart rate and the processor calculates differential changes in the patient's activity data relative to incremental changes in the patient's heart rate.

19. The system as recited in claim 17, wherein the physiologic sensor measures data corresponding to the patient's activity level in response to the patient's intrinsic heart rate and the processor calculates differential changes in the patient's activity data relative to incremental changes in the patient's intrinsic heart rate.

20. The system as recited in claim 19, wherein the processor averages the patient's activity data for selected intrinsic heart rate changes.

21. The system as recited in claim 17, wherein the physiologic sensor includes an activity sensor.

22. The system as recited in claim 21, wherein the activity sensor includes an accelerometer.

23. The system as recited in claim 17, wherein the physiologic sensor further includes a sensor for measuring a patient's respiratory minute ventilation.

24. The system as recited in claim 17, wherein the physiologic sensor includes one or more sensors that measure one or more of oxygen content of blood, pressure, cardiac output, ejection fraction, stroke volume, end diastolic volume, end systolic volume, respiration rate and/or minute ventilation, pH of blood, or ventricular gradient.

25. A method for automatically monitoring the progression of a patient's cardiac condition, comprising:

measuring the patient's intrinsic heart rate;

measuring the patient's activity data;

storing the patient's activity data with respect to the patient's heart rate, the patient's activity data stored in response to a change in the patient's heart rate;

calculating differential changes in the patient's activity data relative to incremental changes in the patient's heart rate; and correlating the differential changes to the progression of the patient's cardiac condition.

* * * * *